United States Patent [19]
Kirk et al.

[11] Patent Number: 5,649,576
[45] Date of Patent: Jul. 22, 1997

[54] PARTITIONING DEVICE

[75] Inventors: Gregory L. Kirk, Skillman, N.J.; Joseph J. Brzezinski, Jr., Bangor; Daniel Chelsky, Moylan, both of Pa.; Thirleen G. Nichols, Winterville, N.C.; T. C. Ramaraj, Dayton, N.J.

[73] Assignee: Pharmacopeia, Inc., Princeton, N.J.

[21] Appl. No.: 606,573

[22] Filed: Feb. 26, 1996

[51] Int. Cl.$^6$ ................................... B65B 1/04
[52] U.S. Cl. .................. 141/129; 141/100; 141/192; 141/279; 222/71; 250/222.2; 377/10
[58] Field of Search ................. 141/1, 9, 31, 67, 141/94, 129, 130, 135, 100, 153, 183, 192, 270, 279; 221/7; 222/40, 52, 71; 356/336; 250/222.2, 559.41; 377/10

[56] References Cited

U.S. PATENT DOCUMENTS

| | | |
|---|---|---|
| 3,710,933 | 1/1973 | Fulwyler et al. . |
| 4,173,415 | 11/1979 | Wyatt . |
| 4,318,480 | 3/1982 | Lombardo et al. ............ 250/222.2 |
| 4,606,631 | 8/1986 | Anno et al. . |
| 4,655,265 | 4/1987 | Duteurtre et al. . |
| 4,680,977 | 7/1987 | Conero et al. . |
| 5,142,140 | 8/1992 | Yamazaki et al. . |
| 5,166,537 | 11/1992 | Horiuchi et al. . |
| 5,286,452 | 2/1994 | Hansen . |

FOREIGN PATENT DOCUMENTS

| | | |
|---|---|---|
| WO93/06121 | 4/1993 | WIPO . |
| WO94/08051 | 4/1994 | WIPO . |

Primary Examiner—Henry J. Recla
Assistant Examiner—Steven O. Douglas
Attorney, Agent, or Firm—Ronald B. Goldstein

[57] ABSTRACT

A system which precisely arrays small objects into a plurality of containers which comprises a vessel containing the objects in a fluid suspension; a tube, the proximal end of which is positioned substantially at the bottom of the vessel and the distal end of which is connected to a member which directs gravitationally-formed fluid drops from the distal end downward into a container positioned below said distal end; a small-objects detector, for detecting the objects in the fluid in the tube, disposed near the distal end; a drop detector connected to the member below the distal end; a device for controlling flow of the suspension through the tube by pressurizing the vessel; or device for discriminating between those signals from the small-objects detector caused by the small objects and those signals caused by other events, i.e., not caused by the small objects; a device for comparing signals from the small-objects detector caused by the small objects with signals from the drop detector; and a device for determining the number of the objects deposited into the container. The system further comprises a positioning device for re-positioning the distal end of the tube from one to another, with timing derived from the small-objects and drop detectors. The positioning device comprises an X-Y transport which is either 1) a movable member which moves the distal end of the tube and the detectors or 2) an X-Y stage which moves the containers, with the tube and the detectors attached to a stationary member.

25 Claims, 6 Drawing Sheets

PARTITIONING DEVICE

BACKGROUND OF THE INVENTION

There is interest in methods for the synthesis of large numbers of diverse compounds that can be screened for various possible physiological or other activities. Techniques have been developed in which one adds individual units sequentially as part of the chemical synthesis to produce all or a substantial number of the possible compounds which can result from all the different choices possible at each sequential stage of the synthesis. WO 93/06121, Apr. 1, 1993, teaches methods for solid support-based synthesis of random oligomers wherein identification tags on the solid supports are used to facilitate identification of the oligomer sequence synthesized. A detachable tagging system is described in Still et al., WO 94/08051, Apr. 14, 1994, which teaches the synthesis of large combinatorial libraries of compounds attached to solid supports.

In order to screen the compounds produced by these new synthetic methods, it is desirable to partition from a pool containing very large (up to the range $10^6$–$10^9$) numbers of solid supports into collection plates with wells, typically 96 wells containing 1–30 supports per well. These solid supports, commercially available as beads, are generally 50–1000 µm in diameter. The number of beads per well is a matter of choice, but should be at least one and not greater than 200, constrained by screening statistics, solubility factors, or size. Furthermore, the number per well should be consistent. Therefore, no well should be empty. However, an average variation of ±5 beads per well is acceptable for wells containing 20 beads. When single beads are to be screened in each well, it is desirable to minimize empty wells while avoiding multiple beads per well in order to avoid the need for rescreening these beads.

Various devices are known in the art which sort particles from liquid suspensions. For example, U.S. Pat. No. 3,710,933, Fulwyler et al., describes a particle sorter applicable to the sorting of biological cells which analyzes cells in a flow chamber and then produces cell-containing droplets via a piezoelectric crystal. Emerging droplets are sorted into two receptacles. Droplets containing selected cells are electronically charged and then deflected by a static electric field into one receptacle. Unselected cells drop into the other receptacle. U.S. Pat. No. 4,173,415, Wyatt, describes an apparatus for characterizing organic cells such as leukocytes which creates an aerosol from a cell suspension to produce a series of droplets which are then divided into cell-containing and non-cell-containing streams. The cell-containing stream is then air-dried and the cells finally analyzed by monochromatic light. U.S. Pat. No. 4,606,631, Anno et al., describes a particle counter which utilizes a flowing sheath solution to surround the sample solution which contains the particles, typically blood corpuscles, to be counted. U.S. Pat. No. 4,680,977, Conero et al., teaches an apparatus for sensing the flow of a liquid by detecting and measuring drops through an optical drip chamber. U.S. Pat. No. 4,655,265, Duteurtre et al., describes an apparatus for the batch transfer of brittle particles, specifically yeast-containing alginate beads, from a suspension into fermentation containers. U.S. Pat. No. 5,142,140, Yamazaki et al., describes an apparatus which uses a polarized beam splitter for counting particles, typically leukocytes, suspended in a fluid. U.S. Pat. No. 5,166,537, Horiuchi et al., describes an improved Coulter Counter device which utilizes a light detection method in combination with an electric impedance method and compares the signals therefrom to exclude false data obtained from multiple particles being present simultaneously. U.S. Pat. No. 5,286,452, Hansen, teaches a method for analyzing multiple analytes in a single fluid sample and a sheath-type flow cell for performing said method. None of these methods and teachings are suitable for accurately counting a number of small objects, including beads in the size range mentioned above removed from a fluid reservoir, and depositing all or a pre-selected number of them into one or multiple containers in the form of droplets.

SUMMARY OF THE INVENTION

A device has now been made which identifies and counts small solid objects, and which can precisely array said small objects into one or more containers. The device comprises a vessel containing said objects in a fluid suspension; a tube, the proximal end of which is immersed in said suspension and the distal end of which is connected to a member which directs gravitationally-formed fluid drops from said distal end downward into a container positioned below said distal end; a small-objects detector, for detecting said objects in the fluid in the tube, disposed near said distal end; a drop detector connected to said member below said distal end; means for controlling flow of said suspension through said tube; means for discriminating between those signals from said small-objects detector caused by said small objects and those signals caused by other events, i.e., not caused by said small objects; means for comparing signals from said small-objects detector caused by said small objects with signals from said drop detector; and means for determining the number of said objects deposited into said container. Preferably the proximal end of said tube is positioned substantially at the bottom of said vessel. Also, preferably the means for controlling flow of said suspension through said tube is by pressurizing said vessel. The device further comprises positioning means for re-positioning the distal end of said tube from one said container to another said container, with timing derived from said small-objects and drop detectors. The positioning means comprises an X-Y transport which is either 1) a movable member which moves the distal end of said tube and said detectors or 2) an X-Y stage which moves the containers, with said tube and said detectors attached to a stationary member. Another embodiment of the invention enables removal of drops as they fall from the tube to said containers. This assures that selected drops contain a single bead without debris or fragments. This modification also avoids delivery of multiple-object containing drops in the single object/container application. Evaluation of a drop for acceptability is determined electronically while the drop is in flight.

DESCRIPTION OF THE PREFERRED EMBODIMENTS

An embodiment of the invention is an apparatus for precisely arraying small solid objects into a plurality of containers, which comprises:

a vessel containing small solid objects in a fluid suspension;

a tube, the proximal end of which is immersed in said suspension and preferably is positioned substantially at the bottom of said vessel, said tube being adapted for transport of fluid from said vessel;

a member, connected to the distal end of said tube, adapted for directing gravitationally-formed fluid drops from said distal end downward to be deposited into a plurality of containers positioned below said distal end;

a small-objects detector, adapted for detecting said objects in the fluid in said tube, disposed near said distal end;

a drop detector attached to said member below said distal end; means for controlling flow of said suspension through said tube, preferably by pressurizing said vessel;

means for discriminating between signals from said small-objects detector caused by said objects and signals not caused by said objects;

means for comparing signals from said small-objects detector caused by said small objects with signals from said drop detector;

means for determining the number of said objects deposited into each of said containers;

means for re-positioning the distal end of said tube from one said container to another said container; and means for timing said re-positioning with respect to signals from said drop detector, said small-objects detector, or the combination thereof.

Another embodiment of the invention is a method for precisely arraying small solid objects into a plurality of containers, which comprises:

providing said objects in a fluid suspension;

transporting said fluid suspension, at a controlled rate, to a small-objects detector;

discriminating between signals from said small-objects detector caused by said objects and signals not caused by said objects;

allowing discrete fluid drops to form due to action of gravitational forces upon said fluid suspension;

allowing said discrete drops to fall, due to action of said gravitational forces;

providing a drop detector in the path of the falling drops;

comparing signals from said drop detector with signals from said small-objects detector caused by said objects, so as to determine the number of said objects in each drop;

directing said drops into a container;

redirecting said drops into a different container, based on signals from said drop detector, signals from said small-objects detector, or signals from both such detectors indicating that a desired number of said small objects have been directed into the previous container; and repeating said redirecting step.

Figure 1:
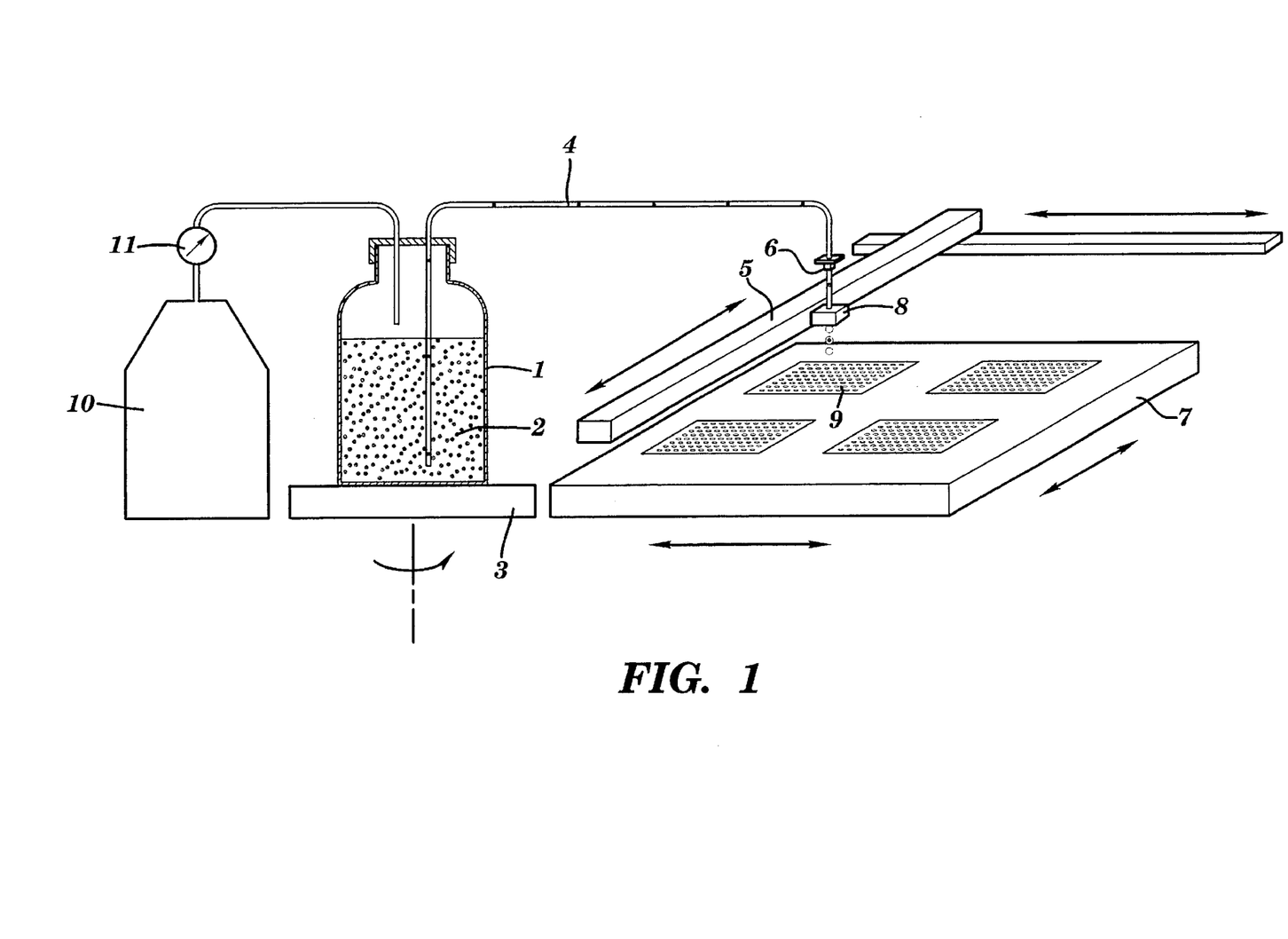
FIG. 1 is a general drawing of the invention indicating its principal components with movable X-Y arm or platform.

Referring to FIG. 1, a sealable vessel 1 containing an isobuoyant suspension of the small solid objects (e.g., beads) 2 to be sorted is placed on an orbital shaker 3. The inside, lower surface of the vessel is preferably concave or has a depressed area to facilitate removal of the maximum number of beads. The beads generally are those suitable for combinatorial libraries, i.e., the combinatorial synthesis of diverse compounds, as described, for example, in Still et al., WO 94/08051. Such combinatorial libraries may comprise very large numbers (0.01–1.5 million) of different members each represented in a redundancy of up to 1000.

Generally, the beads are about 50–1000 μm in diameter and have a rigid or semi-rigid surface. They include cellulose beads, controlled pore-glass beads, silica gels, polystyrene beads optionally cross-linked with divinylbenzene and optionally grafted with polyethylene glycol and optionally functionalized with amino, hydroxy, carboxy, or halo groups, grafted co-poly beads, poly-acrylamide beads, latex beads, dimethylacrylamide beads optionally cross-linked with N,N'-bis-acryloyl ethylene diamine, glass particles coated with hydrophobic polymer, etc. Preferably, the beads are divinylbenzene-cross-linked, polyethyleneglycol-grafted polystyrene beads optionally functionalized with amino groups (for example, TentaGel® S $NH_2$, Rapp Polymere). The beads in any batch are of approximately equal size, i.e., having a range no greater than 2× difference in diameter. Typically, the beads have been through a process of combinatorial synthesis such as described in Still et al. (supra); i.e., the beads may have attached to them the synthesized compounds, the tagging molecules, or both.

Ideally, the beads are maintained in a uniform random suspension in the vessel so that any volume sampled by the tube contains the same statistical distribution of bead count. Aggregated beads are especially undesirable when arraying plates in a single-bead-per-well format. To keep the beads separated from one another and to ensure an isobuoyant suspension and proper flow of the suspension through the tube and, ultimately, proper drop formation, the beads are suspended by gentle agitation in a liquid which is chemically inert, non-corrosive to tube 4, and has a room temperature viscosity in the range 0.500–4.000 mPa-sec, a surface energy in the range 15–65 $mJ/m^2$, and a density in the range of 1.00–1.50 $g/cm^3$. Typical such suspending liquids are trichloroethane/isopropanol (TCE/IPA) mixtures in proportions ranging from about 70–90:30–10 by volume and water/KBr/isopropanol mixtures in proportions ranging from about 35–45:35–45:15–25 by weight. In these mixtures the IPA is a surfactant additive which helps avoid bead clumping or aggregation to further ensure a uniform random sampling of beads. The volatile TCE/IPA mixture is useful when the container is to be rapidly dried after bead sorting. However, the choice of volatiles as suspending liquids is constrained because of their possible residues and incompatibilities with the container materials (e.g., plastics). The water/KBr/IPA mixture is useful when a liquid compatible with most plastics is desired. The water/KBr/IPA mixture can be rinsed through the containers if the containers have porous bottoms that retain beads. A two-step cleaning process involves rinsing the containers with 2–5 water wash steps followed by a single IPA wash step. The end result should be a residue-free collection of beads in each container.

Agitation of the suspension can be eliminated if its viscosity is sufficiently high. For example, an agitated suspension (not necessarily isobuoyant) of beads in an aqueous solution of agarose (ca. 0.05%) will become quite viscous when cooled to room temperature from about 40° C. The viscosity of the cooled suspension is so high that the beads will remain in their uniformly random state without further agitation during sampling. Other commercially available thickening agents such as alginate and xanthan gum may also be useful. It is important in most cases to remove the additive that causes the viscosity by filtering, as through the porous bottoms described above. This may require some reversibility in viscosity. For example, the containers can be heated to 40° C. to allow the agarose to become thin enough to wash out. In other cases dilution, possibly with acid or base treatment, may cause the solution to become more readily removed. If the need for agitation is eliminated, then the suspension vessel 1 can be attached directly to and above arm 5. In this case tube 4 is substantially shorter than the 1.00–2.00 m described below.

A single, seamless, thin-wall, flexible, optically clear tube 4, the proximal end of which is positioned substantially at the bottom of vessel 1 to facilitate removal of the maximum amount of suspension from the vessel, connects the vessel to an arm or member 5. By "optically clear" is meant that the wall of the tube readily permits transmission of radiation at the wavelength utilized by the small-objects detector. The tube is composed of an inert or non-stick material such as Teflon (polytetrafluoroethylene), has an inside diameter of 200–4000 μm, and a length of 1.0–2.0 m, of which approximately 24 mm (i.e., the length of the tube which would accommodate one drop of fluid) extends through and beyond optical bead detector 6. The inside diameter of the tube is chosen to be approximately twice the diameter of the largest bead. There are no joints, kinks, or valves from the point the beads enter the tube within the vessel to the point they exit the tube at the distal end in the form of drops. This avoids any lodging of beads, bead fragments, or foreign matter that could interrupt the flow of beads. The drops of this invention form by gravitational forces; i.e., unlike those of, for example, U.S. Pat. No. 3,710,933, which are produced by a piezoelectric transducer, the present drops have essentially zero velocity at the time of their release from tube 4. As used herein, by "gravitational forces" is meant any method whereby the size of a drop is comparable to that formed by the force of gravity alone; e.g., vibrational release of a nearly formed drop.

The arm 5 may be movable, in which case it is activated by an X-Y transport which positions the distal end of tube 4, the bead detector 6, and the drop detector 8 over a plurality of stationary collection containers 9. A suitable collection device for this embodiment is the commercially available Gilson FC204 fraction collector (Gilson Medical Electronics, Inc.). Alternatively, the containers can be moved under a stationary arm 5 by means of a movable X-Y stage 7. Such containers may be bottles, tubes, vials, reaction vessels, the individual wells of a multi-well collector, such as a commercially available 96-well plate (Millipore or NUNC), or other containers suitable for collecting beads. The 96-well plates have solid or porous bottoms (e.g., Millipore Multi Screen BV plates with 1.2 μm low-binding PVDF membranes).

Drop detector 8 is attached to arm 5 below the distal end of tube 4 (and therefore below the bead detector 6) such that the drop detector is in the path of the drops as they fall, due to gravitational forces, off the distal end of the tube 4. The X-Y transport 7 centers the individual containers beneath the falling drops, with the plane of X-Y motion and the surface that supports the containers substantially perpendicular to the drop path.

Positive pressure is maintained above the isobuoyant suspension from a source of compressed air 10, preferably an inert gas such as $N_2$, by a regulator and valve 11. Alternative methods of maintaining a satisfactory flow rate are also possible. For example, if vessel 1 has flexible walls or a movable wall member, flow can be controlled by reducing its volume; i.e., by controllably squeezing the flexible walls of the vessel or driving said movable wall as by a piston. The pressure is determined empirically, such that a flow rate of about 60 drops/min is achieved at the distal end of tube 4. Such a relatively slow flow rate permits time to count the drops, move the X-Y transport when necessary, and deflect non-bead-containing drops. Ideally, the pressure is sufficiently above atmospheric pressure so that changes in ambient pressure over an eight-hour period do not significantly affect the flow rate. Note that flow rate of the suspension is inversely related to its viscosity. Drop volumes are in the range 5–40 μL per drop. This allows a plurality of drops to be deposited into each container before it is necessary to redirect the drops to the next container. For example, a 96-well plate with 200 μL wells allows 1–40 drops per well.

Figure 2:
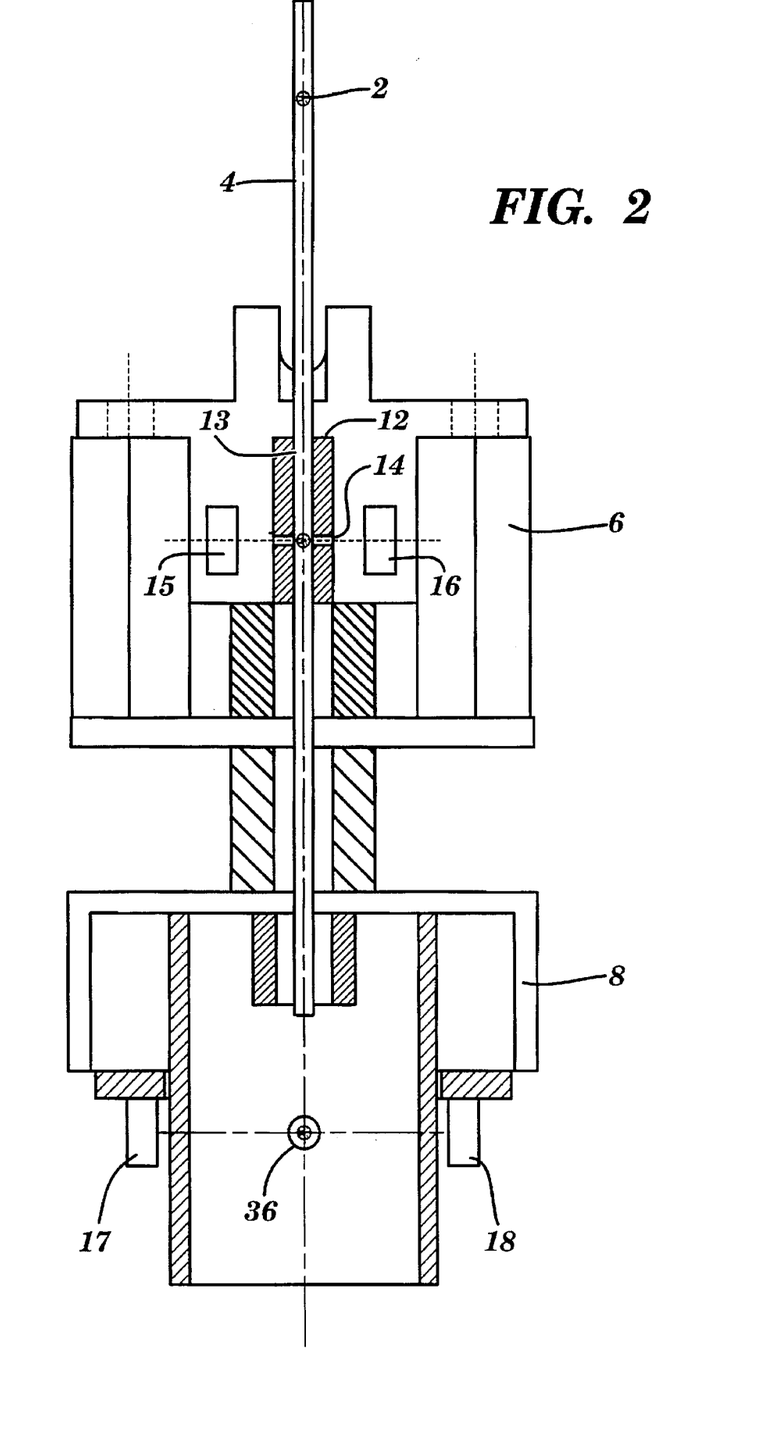
FIG. 2 is a drawing of the small-objects and drop detectors.

Referring to FIG. 2, an optical bead detector 6 is shown which comprises a collimator block 12 which is substantially optically opaque, said block containing two bores intersecting at right angles. The diameter of the first, substantially perpendicular bore 13, is such as to snugly allow passage of tube 4. The diameter of the second bore 14 is substantially identical to the inside diameter of tube 4. One side of bore 14 contains a radiation source 15 and the other side a suitable radiation detector 16. The radiation source may be any convenient source, preferably an infra-red light-emitting diode. When an optical bead detector is used, tube 4 is preferably optically clear at the detection wavelength.

Alternative bead detectors are also within the scope of the invention. The functional requirement is for the detector to generate a distinct signal when a bead has moved past the detection area, which is a short (<3 mm) segment of the tube near its distal end. The detector must not create obstructions that would slow or trap beads. Some alternatives to optical detectors are:

Ultrasonic detection methods, such as are employed in commercial bubble detectors (ZEVEX, Mass.) for critical small fluid paths (e.g., intravenous drip lines in hospitals), can be used. These devices employ an ultrasonic sound transducer that transmits vibrations across the tube to a detector on the other side of the tube. Any object that crosses between the detector and the transmitter that has sound transmission properties significantly different from those of the suspending liquid (e.g., different compressibility, viscosity, etc.) will create a transient signal in the detector.

Electrical resistance methods may be used which utilize two electrodes fabricated seamlessly in the walls of the tube. The electrical resistance to AC voltage signals between the two electrodes is modulated when a non-conducting bead displaces the conducting salt solution as it travels between the electrodes. Circuitry analogous to that shown for the optical bead detector in FIG. 3 generates an electrical signal during this event. This technology was used in early Coulter Counters (e.g., U.S. Pat. No. 5,166,537).

The drop detector 8 is disposed below bead detector 6 and the distal end of tube 4, and comprises a light source 17 and a suitable light detector 18 located opposite each other and such that drops 36 from tube 4 will intersect a light beam traveling between the two. The light source may be any convenient source, preferably infra-red or laser.

Figure 3:
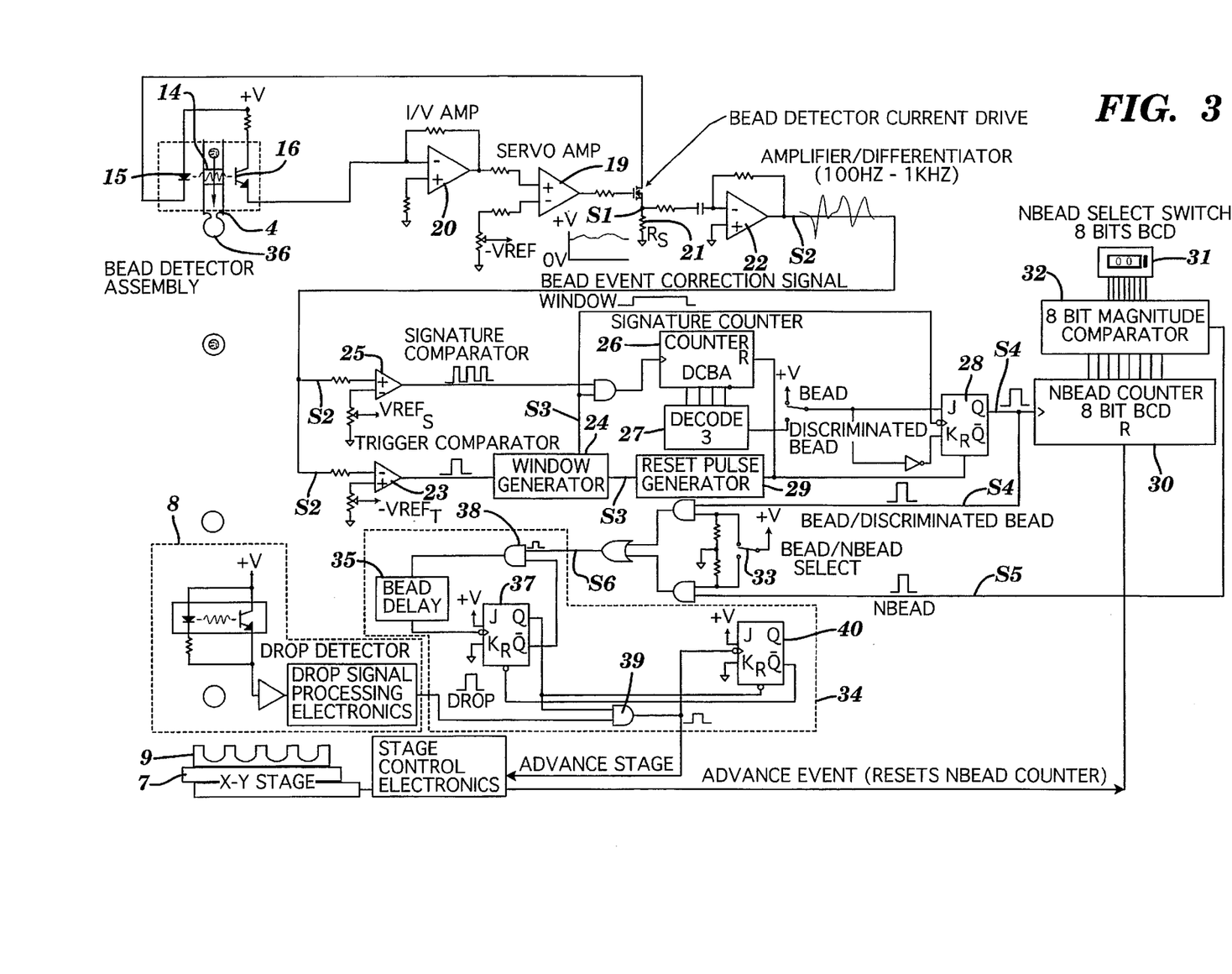
FIG. 3 is a schematic representation of the small object detector, fraction collector, and discriminator logic.

Referring to FIG. 3, generally, bead and non-bead events in the bead detector assembly generate signals which are interpreted by the discrimination algorithm and correlated with signals from a drop detector. The comparison of these signals determines the repositioning of the X-Y transport, which moves the distal end of tube 4 relative to collection containers 9. Specifically, servo amp 19 regulates current through light source 15 to maintain a constant signal in I/V amp 20 from the current in light detector 16. When beads in tube 4 intersect light from source 15, a transient increase in current through light source 15 is caused in order to maintain constant I/V from detector 16. This causes a disturbance in voltage across sense resistor, $R_s$, 21. Collimator hole 14 maximizes the relative change in disturbance signal by maximizing the relative area blocked by the bead while assuring that no bead can be missed.

The disturbance signal S1 is amplified and filtered by differentiator 22 to create an analog voltage signal S2. (See FIG. 4 and the detailed description of signal S2 below.) The filtering selects frequencies in a range typical of bead-caused disturbances for a given bead velocity and size. Bead velocity is determined by drop rate and tube inner diameter. A filtering frequency range of 0.1 to 1 kHz is typical for drop rates of 60 drops/min, average bead diameters of 200 μm, and tube inner diameter of 500 μm. When signal S2 reaches $-Vref_t$ at trigger comparator 23 it initiates an event window signal S3 from window generator 24. This window of time, typically 20 to 50 msec, represents the maximum time a bead takes to travel through collimator 14 in its path to the distal end of the tube. Signature comparator 25, counter 26, and decoder 27 comprise a discriminator circuit that allows confirmation that signal S2 represents a true bead signal. In that event, a bead pulse S4 is generated at the end of window signal S3.

An effective bead discrimination algorithm has been developed that counts signature threshold crossings by S2 within an event window after trigger threshold. This bead discrimination algorithm is implemented using discrete logic components. When the initial negative going portion of the waveform reaches the trigger threshold ($-Vref_t$) at trigger comparator 23, an event window signal S3 is generated by window generator 24. The duration of this window is set to be about the longest time that a disturbance signal would last if caused by a bead. During the window signal, counter 26 is enabled and signature comparator 25 outputs a pulse whenever a positive going transition of the waveform reaches the signature threshold ($Vref_s$). The pulses from signature comparator 25 increment counter 26. Decoder 27 polls the output of counter 26 for a "2" or a "3," which would be indicative of the signature of a bead (see FIG. 4(c)). If this condition is satisfied, then bead flip-flop 28 is enabled. In this case, on the falling edge of the event window S3, bead pulse S4 is initiated and then ended by reset pulse generator 29. This reset pulse also clears counter 26.

The signature logic can be disabled by permanently enabling bead flip-flop 28. In this way all events detected by trigger comparator 23 generate bead detection pulses S4 independently of the signature, i.e., regardless of the characteristics of each event. This is effectively a pulse height discrimination algorithm, as compared with the algorithm based on pulse height and shape described above. Bead counter 30 is incremented by bead pulses S4. User-selectable thumbwheel switch 31 programs magnitude comparator 32 to generate an n-bead pulse S5 each time the desired count is reached.

Once the desired number of beads has been counted, it is the function of state machine 34 (which is the collective term for devices 35, 37, 38, 39, and 40) to synchronize the movement of the X-Y transport with the fall of the correct drop. For example, if no more than 10 beads per container are to be permitted, the X-Y transport moves so as to direct drops into a new container immediately after the drop containing the tenth bead has fallen into the previous container. Selector switch 33 allows the user to trigger state machine 34 by bead pulses S4 or n-bead pulses S5, respectively, for single-bead-per-container or multiple-beads-per-container settings. State machine trigger signal S6 passes through gate 38 and triggers bead delay 35. This delay period, typically 50 to 500 msec, corresponds to the time required for the bead causing the trigger event at collimator hole 14 to travel to the end of tube 4 to be contained in a forming drop 36, such time being determined by flow rate, inner diameter and tube length beyond the collimator. At the end of this delay, drop flip-flop 37 is toggled, disabling future triggers through gate 38. Drop flip-flop 37 also enables drop signal S7 from drop detector 8 through drop gate 39 to toggle reset flip-flop 40 and reposition the end of tube 4 over the next container by activating the X-Y transport for either the movable arm 5 or movable platform 7. This assures relative motion only when there is no danger of shaking a drop off tube 4. Reset flip-flop 40 resets state machine 34 to be prepared for the next trigger event. Upon completion of its movement, the X-Y transport creates a reset signal S8 to clear bead counter 30.

Figure 4A:
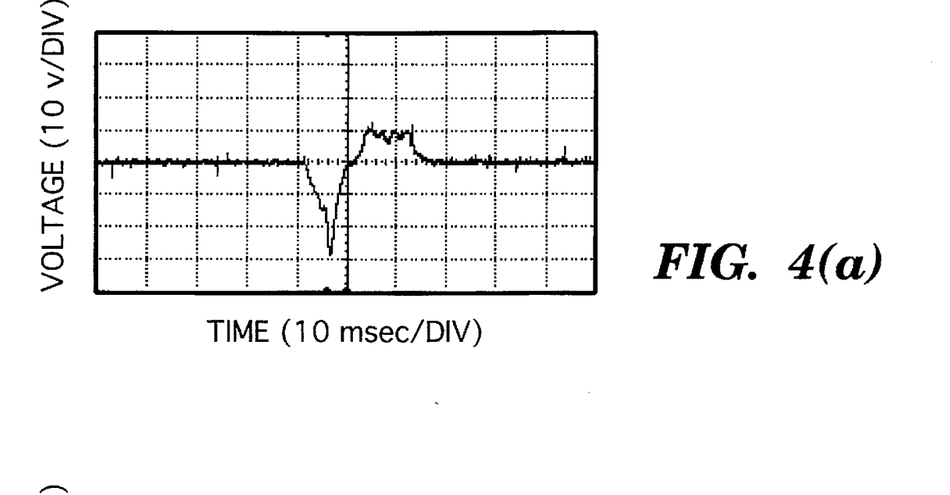
FIG. 4(a)–4(e) contain electrical bead disturbance wave forms captured from an oscilloscope. These wave forms correspond to Signal S2 in FIG. 3. Threshold levels and event window time periods are shown superimposed.
Figure 4B:
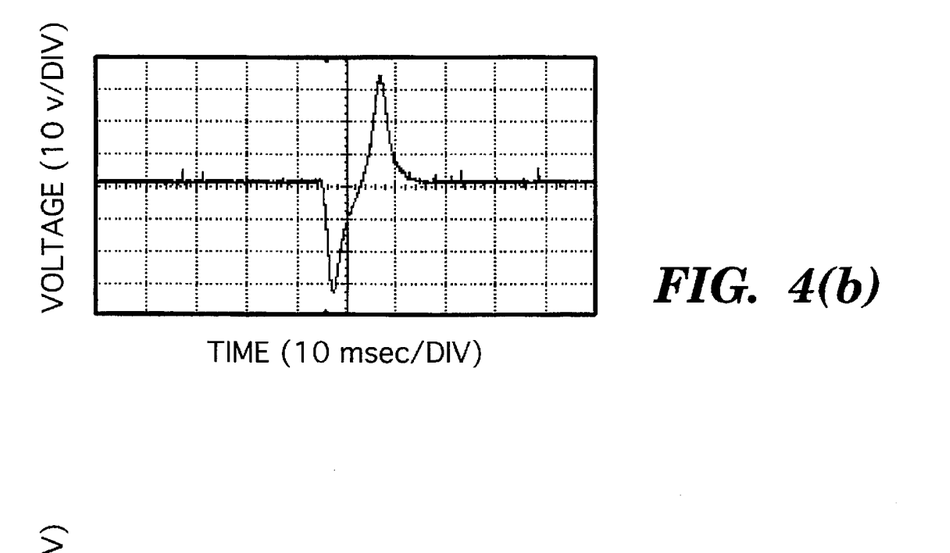
Figure 4C:
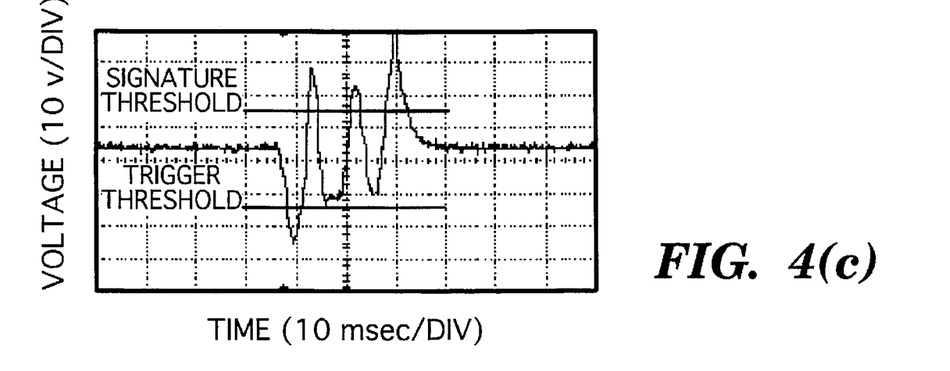
Figure 4D:
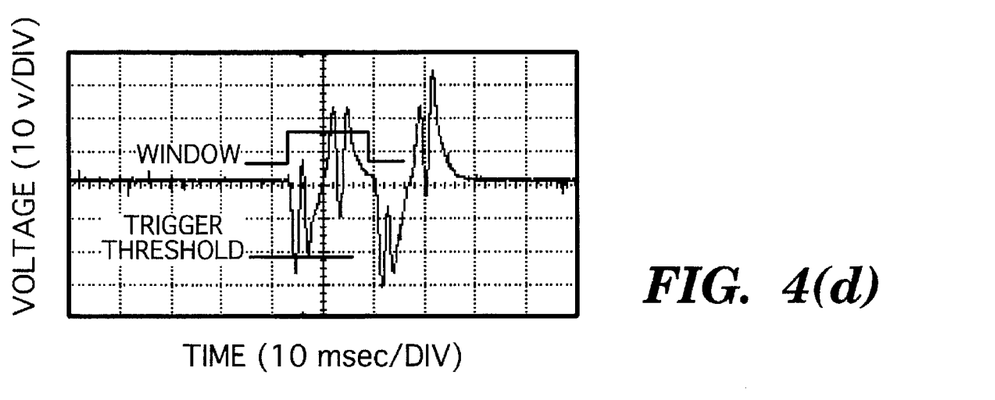
Figure 4E:
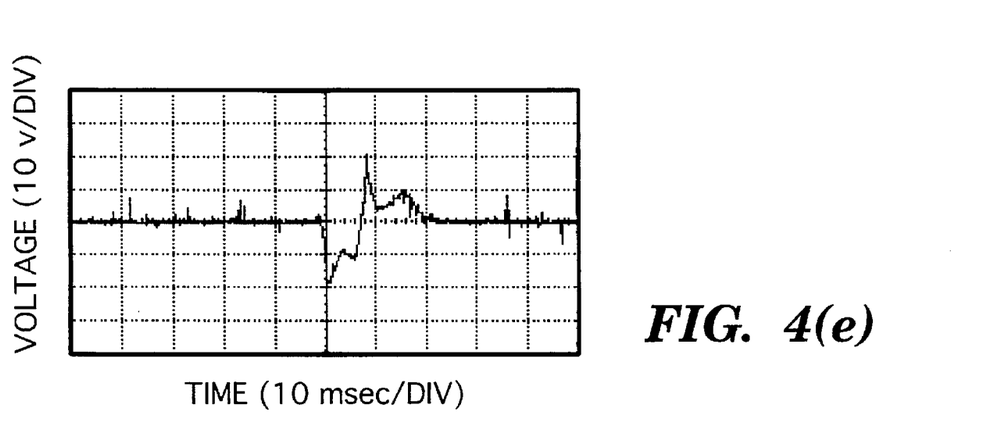

FIG. 4(a)–4(e) is a compilation of various S2 signals (voltage vs. time) generated by both bead and non-bead (i.e., bubble, debris, or bead fragment) events that generate an event window signal S3 through comparator 23. FIG. 4(c) is a typical waveform of a single bead with trigger threshold ($-Vref_t$) and signature threshold ($Vref_s$) levels superimposed. The S2 signal for bubbles (FIG. 4(b)), fibers (FIG. 4(e)), and bead fragments (FIG. 4(a)) are clearly qualitatively different from typical bead signals. The method of discriminating bead from non-bead events focuses on the number of major oscillations typical for these signals. Using FIG. 4(c) as a reference, bead event signals typically cross the signature threshold three times. In fact, occasional bead event signals (e.g., FIG. 4(d)) are asymmetrically offset, resulting in only two crossings. Typical bubble events result in only one crossing. Bead fragments and fibers create variable signals, with fewer than two or more than three crossings, respectively. The variable low levels associated with these signals can be further discriminated by setting the signature threshold suitably high. This level can be determined by observing typical bead signals and setting the threshold accordingly.

Figure 5:
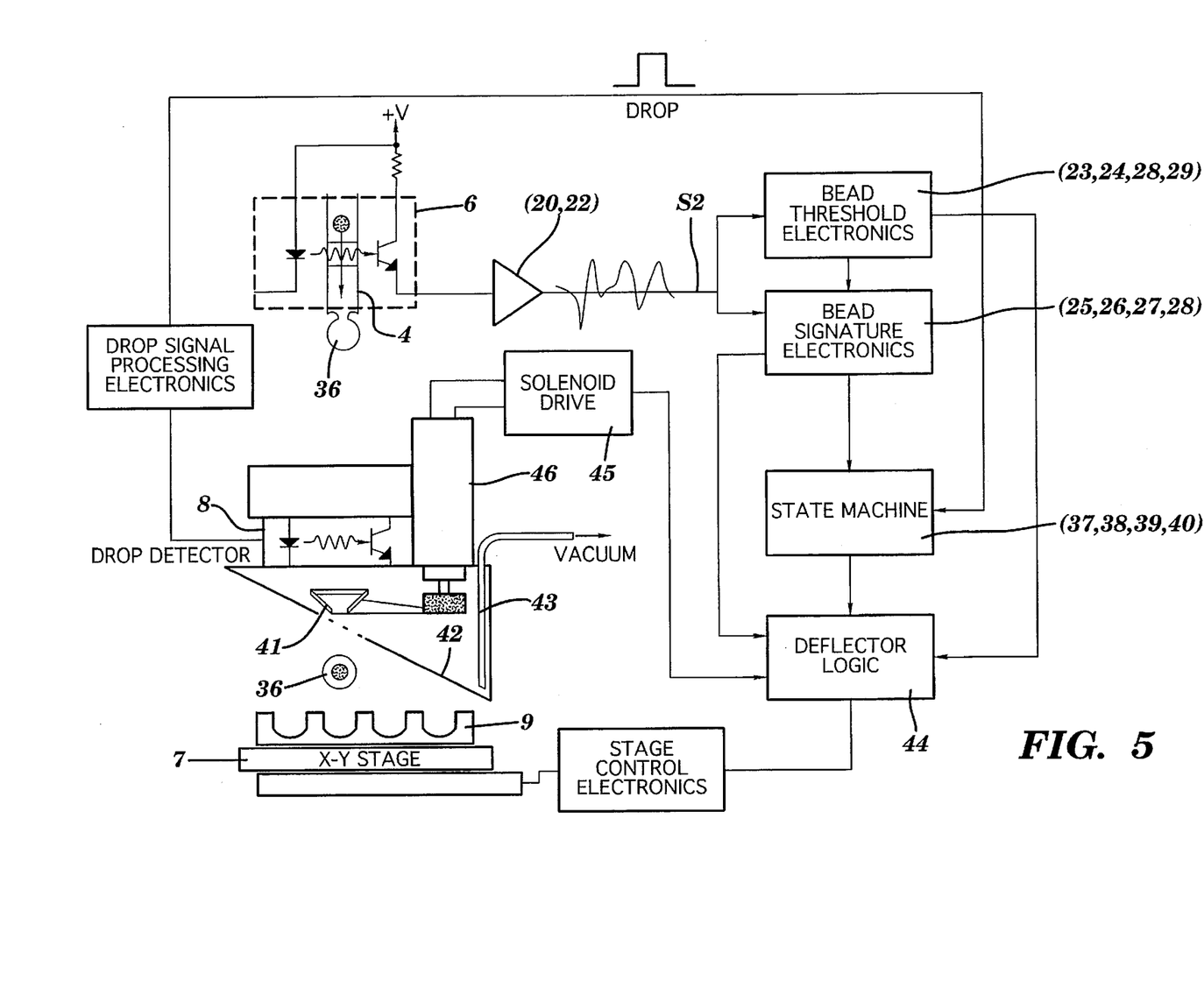
FIG. 5 is a schematic representation of a preferred system shown with drop deflector and additional deflector logic.

Referring to FIG. 5, another embodiment of the invention is shown that enables drops to be re-directed from their path to the container 9 by a deflector 41. These unwanted drops are caught by a collection trap 42 where the fluid and debris are removed through a vacuum sump pump 43. Thus, only drops containing beads, but not debris or bead fragments (or multiple beads, in the single-bead-per-container setting), are allowed to accumulate in a given container. This is advantageous in the single-bead-per-container setting by avoiding cases where multiple beads (see FIG. 4(d)) are delivered to a container or where the container is filled with liquid before any bead is delivered. In either multiple- or single-bead-per-container settings, this embodiment is advantageous by removing instances of debris or bead fragment-containing drops in a container. Where a drop is deflected due to the undesirable presence of multiple beads therein, the present invention contemplates that such multiple-bead-containing drops may be collected and recycled to vessel 1.

The decision to deflect or deliver a given drop to a container must be made after the drop has been released from the end of tube 4 and detected in-flight by drop detector 8, since the information necessary to decide is not complete until that time. Bead threshold electronics (23, 24, 28, 29) initiate the event of detecting a bead as described above. Bead signature electronics (25, 26, 27, 28, 29) discriminate between bead and non-bead events as described above.

Deflector logic 44 is alerted by any event triggered by the bead threshold electronics and is prepared to advance the X-Y transport upon completion of the upcoming drop event. Bead authenticity information with respect to the alerting event and all subsequent events is also provided to the deflector logic 44 by the bead signature electronics. The state machine 34 provides a timing pulse to the deflector logic 44 when the drop containing the initiating bead is in flight. Deflector logic 44 can now determine whether that drop is acceptable based on the timely information described above. If the drop in question is acceptable (i.e., is determined to contain only beads or a single bead), then the deflector logic activates the solenoid drive 45 to move the deflector 41 out of the path of the drop, so as to complete the drop event. The time taken to accept the drop and activate the solenoid is in the range of 2 to 15 msec, based on the flight time of the drop and the position of the deflector. This is easily achieved by standard digital electronics and electromechanical actuators of the appropriate size and weight. Device 46 is a rotary solenoid-based actuator that moves deflectors by rotation caused by electrical current.

Although the invention has been disclosed with reference to the embodiments depicted herein, it will be apparent to one of ordinary skill in the art that various modifications and substitutions may be made to such embodiments. Any such modifications and/or substitutions are intended to be within the scope of the invention as defined by the following claims.

What is claimed is:

1. An apparatus for precisely arraying small solid objects into a plurality of containers, which comprises:

a vessel containing small solid objects in a fluid suspension;

a tube, the proximal end of which is immersed in said suspension, said tube being adapted for transport of fluid from said vessel;

a member, connected to the distal end of said tube, adapted for directing gravitationally-formed fluid drops from said distal end downward to be deposited into a plurality of containers positioned below said distal end;

a small-objects detector, adapted for detecting said objects in the fluid in said tube, disposed near said distal end;

a drop detector attached to said member below said distal end;

means for controlling flow of said suspension through said tube;

means for discriminating between signals from said small-objects detector caused by said objects and signals not caused by said objects;

means for comparing signals from said small-objects detector caused by said small objects with signals from said drop detector;

means for determining the number of said objects deposited into each of said containers;

means for re-positioning the distal end of said tube from one said container to another said container; and means for timing said re-positioning with respect to signals from said drop detector, said small-objects detector, or the combination thereof.

2. An apparatus of claim 1 wherein the objects in said vessel are in an in agitated, isobuoyant fluid suspension.

3. An apparatus of claim 2 wherein said isobuoyant fluid suspension has a room temperature viscosity in the range 0.500–4.000 mPasec, a surface energy in the range 15–65 mJ/m$^2$, and a density in the range of 1.00–1.50 g/cm$^3$.

4. An apparatus of claim 3 wherein said isobuoyant fluid is trichloroethane/isopropanol (TCE/IPA) in the range 70–90:30–10 by volume or water/KBr/isopropanol in the range 35–45:35–45:15–25 by weight.

5. An apparatus of claim 1 wherein said tube is flexible and optically clear at the wavelength of the radiation utilized by said small-objects detector.

6. An apparatus of claim 5 wherein said tube has an inside diameter of 200–4000 μm, and a length of 1.0–2.0 m.

7. An apparatus of claim 1 wherein the means for controlling flow of said suspension through said tube include pressurizing said vessel.

8. An apparatus of claim 7 wherein said means for controlling flow is compressed gas.

9. An apparatus of claim 1 wherein the proximal end of said tube is positioned substantially at the bottom of said vessel.

10. An apparatus of claim 1 wherein said small-objects detector comprises an optical detector and a collimator block.

11. An apparatus of claim 1 wherein said objects are about 50–1000 μm in diameter and are cellulose beads, controlled pore-glass beads, silica gels, polystyrene beads optionally cross-linked with divinylbenzene and optionally grafted with polyethylene glycol and optionally functionalized with amino, hydroxy, carboxy, or halo groups, grafted co-poly beads, poly-acrylamide beads, latex beads, dimethylacrylamide beads optionally cross-linked with N,N'-bis-acryloyl ethylene diamine, or glass particles coated with hydrophobic polymer.

12. An apparatus of claim 1 wherein said means for repositioning the distal end of said tube comprises an X-Y transport which is either (i) a movable member which moves the distal end of said tube and said detectors; or (ii) an X-Y stage which moves the containers, wherein said tube and said detectors are attached to a stationary member.

13. An apparatus of claim 1 further comprising a drop deflector for removal of drops as they fall from said tube to said containers.

14. A method for precisely arraying small solid objects into a plurality of containers, which comprises:

providing said objects in a fluid suspension;

transporting said fluid suspension, at a controlled rate, to a small-objects detector;

discriminating between signals from said small-objects detector caused by said objects and signals not caused by said objects;

allowing discrete fluid drops to form due to action of gravitational forces upon said fluid suspension;

allowing said discrete drops to fall, due to action of said gravitational forces;

providing a drop detector in the path of the falling drops;

comparing signals from said drop detector with signals from said small-objects detector caused by said objects, so as to determine the number of said objects in each drop;

directing said drops into a container;

redirecting said drops into a different container, based on signals from said drop detector, signals from said small-objects detector, or signals from both such detectors indicating that a desired number of said small objects have been directed into the previous container; and repeating said redirecting step.

15. A method of claim 14 wherein said fluid suspension is an agitated, isobuoyant fluid suspension.

16. A method of claim 15 wherein said isobuoyant fluid suspension has a room temperature viscosity in the range 0.500–4.000 mPasec, a surface energy in the range 15–65 mJ/m$^2$, and a density in the range of 1.00–1.50 g/cm$^3$.

17. A method of claim 16 wherein said isobuoyant fluid is trichloroethane/isopropanol (TCE/IPA) in the range 70–90:30–10 by volume or water/KBr/isopropanol in the range 35–45:35–45:15–25 by weight.

18. A method of claim 14 wherein said transporting of said fluid suspension at a controlled rate is achieved by pressurizing said suspension.

19. A method of claim 18 wherein said pressurizing is achieved with compressed gas.

20. A method of claim 14 wherein said small-objects detector comprises an optical detector and a collimator block.

21. A method of claim 14 wherein said objects are about 50–1000 μm in diameter and are cellulose beads, controlled pore-glass beads, silica gels, polystyrene beads optionally cross-linked with divinylbenzene and optionally grafted with polyethylene glycol and optionally functionalized with amino, hydroxy, carboxy, or halo groups, grafted co-poly beads, poly-acrylamide beads, latex beads, dimethylacrylamide beads optionally cross-linked with N,N'-bis-acryloyl ethylene diamine, or glass particles coated with hydrophobic polymer.

22. A method of claim 14 wherein the controlled rate is about 60 drops/min., and wherein drop volumes are in the range 5–40 μL per drop.

23. A method of claim 14 wherein redirecting said drops is effected with an X-Y transport.

24. A method of claim 14 further comprising deflecting certain drops as they fall, so that the drops are not directed into a container.

25. A method of claim 24 wherein the deflecting occurs after comparing signals from said drop detector with signals from said small-objects detector.

* * * * *